(12) United States Patent
Guo et al.

(10) Patent No.: US 8,137,945 B1
(45) Date of Patent: Mar. 20, 2012

(54) THERMOSTABLE CELLULASE HAVING INCREASED ENZYME ACTIVITY

(75) Inventors: Rey-Ting Guo, Taipei (TW); Ya-Shan Cheng, Taipei (TW); Tzu-Hui Wu, Taipei (TW); Jian-Wen Huang, Taipei (TW); Hui-Lin Lai, Taipei (TW); Cheng-Yen Lin, Taipei (TW)

(73) Assignee: Genozyme Biotech, Inc., Taipei (TW)

( * ) Notice: Subject to any disclaimer, the term of this patent is extended or adjusted under 35 U.S.C. 154(b) by 0 days.

(21) Appl. No.: 13/150,456

(22) Filed: Jun. 1, 2011

(30) Foreign Application Priority Data

Feb. 17, 2011 (TW) .................................. 100105318

(51) Int. Cl.
*C12N 9/42* (2006.01)
*C12N 9/14* (2006.01)
(52) U.S. Cl. ........................................ 435/209; 435/195
(58) Field of Classification Search ........................ None
See application file for complete search history.

*Primary Examiner* — Tekchand Saidha
*Assistant Examiner* — Md. Younus Meah
(74) *Attorney, Agent, or Firm* — Kirton McConkie; Evan R. Witt

(57) ABSTRACT

A thermostable cellulase having increased enzyme activity is disclosed. The cellulase comprises a modified amino acid sequence of SEQ ID NO: 2, wherein the tyrosine at position 61 is substituted with an amino acid selected from the group consisting of phenylalanine, alanine and glycine.

7 Claims, 4 Drawing Sheets

FIG. 1
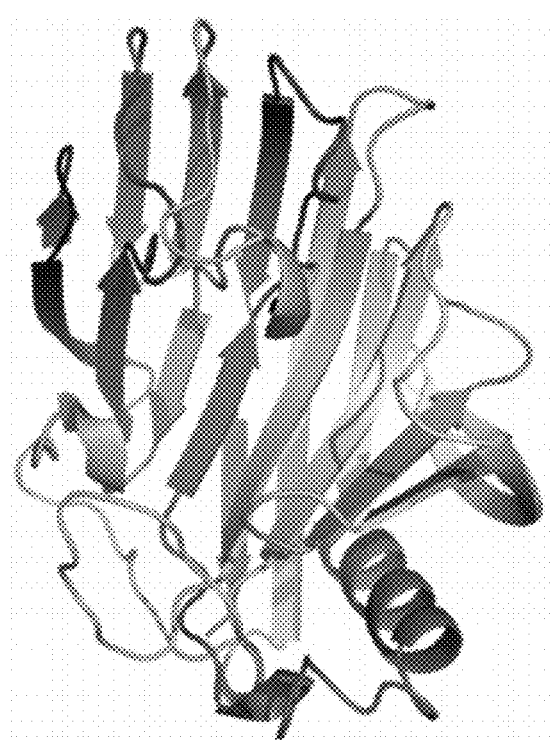
FIG. 2A
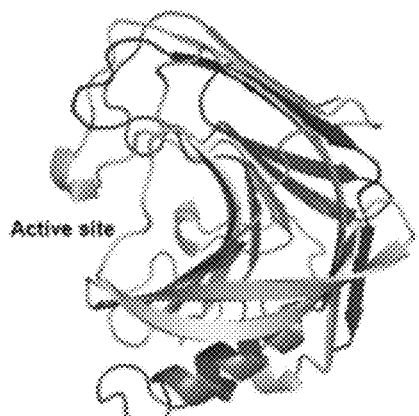
FIG. 2B
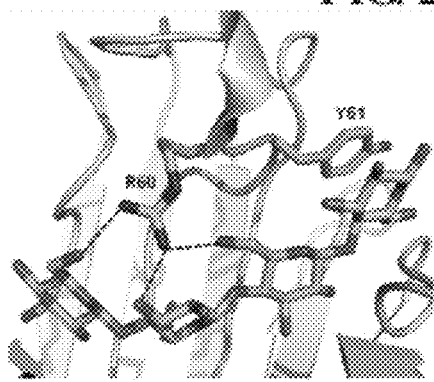
FIG. 2C

| Mutants | Sequences of mutagenic primers |
|---|---|
| Y61F | 5'- TCTCCGAAAGAACCGGAAAGG<u>TTT</u>GTTCTCGGTTATCCCGAGTTT -3' |
| Y61A | 5'- TCTCCGAAAGAACCGGAAAGG<u>GCC</u>GTTCTCGGTTATCCCGAGTTT -3' |
| Y61G | 5'- TCTCCGAAAGAACCGGAAAGG<u>GGT</u>GTTCTCGGTTATCCCGAGTTT -3' |

FIG. 3 atggtactgatgacaaaacgggaacatggattttgtatggaatggcattcgccttcatggagctgaactgtggaacataaagga
 M  V  L  M  T  K  R  E  H  G  F  V  W  N  G  I  R  L  H  G  V  N  L  V  E  H  K  G tactcggttctgtagctatgaaattcgacggtgaaaagataactttcgatgcgtcaattcagaatcttctcccgaaagaaccggaagg
 Y  S  V  L  *  L  *  K  F  D  G  E  K  I  T  F  D  A  S  I  Q  N  L  L  P  K  E  P  E

[t]ttgttctcggttatcccgagttttattacggttacaaaccacggaaaatcaccagcagaaggttcgaaacttccggtacggttcct
 [F] V  L  G  Y  P  E  F  Y  Y  G  Y  K  P  R  K  I  T  S  R  K  V  R  N  F  R  Y  G  S tctatgaaatcatctttcgtcgaagttctttcgatattcacaacgaaccgtctctgcctttgaacttgccatggaaacatggctcaca
 S  M  K  S  S  F  V  E  V  S  F  D  I  H  N  E  P  S  L  P  L  N  P  A  M  E  T  W  L  T gagaaagtacagaaaggaagcattgatggagatgttgaaaatgttctggttctattcaaaaattgcacccgggatgactac
 E  K  V  Q  T  E  A  S  I  G  D  V  E  N  V  W  P  Y  F  K  N  C  T  R  D  D  Y atcgaagagttcaacgaaccgttcgtggtcgaaggagaagtcggagaaccggagctggctgcgtgggcggactgacac
 I  E  E  F  N  E  P  F  V  V  E  G  E  V  E  G  T  R  L  L  A  W  G  D  Y ccgcttccgctgaaggatcccgttgaaggggaagtcgaagctgaaggcatttctgatgccgcggaaagctcttcg
 L  P  F  P  L  K  D  P  V  E  G  R  V  E  A  E  A  F  L  M  P  E  S  L  L agttctgctcgagtgaaagattttgaagatcttactcaccgtctggaaatcggaagcgagttttgaagtcggaaacaaaagtgca
 S  S  A  R  V  K  D  F  E  D  L  T  H  R  L  E  I  G  S  E  F  E  V  G  N  K  S  A caattcggtgagaagttgaaaactctctattgatctgaagctcgaagaatga
 Q  F  G  E  K  F  S  N  F  I  D  L  S  V  R  S  *

-SEQ ID NO: 3
-SEQ ID NO: 4

SEQUENCE LISTING

<160> NUMBER OF SEQ ID NOS: 8

<210> SEQ ID NO 1
<211> LENGTH: 774
<212> TYPE: DNA

-continued

<213> ORGANISM: Thermotoga maritima

<400> SEQUENCE: 1

```
atggtactga tgacaaaacc gggaacatcg gattttgtat ggaatggcat tccccttcc      60
atggagctga atctgtggaa cataaaggaa tactccggtt ctgtagctat gaaattcgac    120
ggtgaaaaga taactttcga tgcggacatt cagaatcttt ctccgaaaga accggaaagg    180
tatgttctcg gttatcccga gttttattac ggttacaaac catgggaaaa tcacacagca    240
gaaggttcga aacttccggt accagtttct tctatgaaat cattttccgt cgaagtttct    300
ttcgatattc accacgaacc gtctctgcct ttgaactttg ccatgaaaac atggctcaca    360
agagaaaagt accagacgga agcatcgatc ggcgatgttg aaatcatggt ctggttctat    420
ttcaacaatc tcacacccgg aggcgaaaag atagaagagt tcacgatccc gttcgtgctg    480
aacggagaga gtgtcgaagg cacctgggaa ctgtggctcg cggagtgggg atgggactac    540
ctcgctttcc gcttgaagga tcccgtgaag aagggaaggg tgaagttcga cgtgaggcat    600
tttcttgatg ccgccggaaa agctctttcg agttctgctc gagtgaaaga ttttgaagat    660
ctttacttca ccgtctggga atcggaacc gagtttggaa gtccggaaac aaaaagtgca    720
cagttcgggt ggaagtttga aaacttctct attgatctgg aggtgagaga atga          774
```

<210> SEQ ID NO 2
<211> LENGTH: 257
<212> TYPE: PRT
<213> ORGANISM: Thermotoga maritima

<400> SEQUENCE: 2

```
Met Val Leu Met Thr Lys Pro Gly Thr Ser Asp Phe Val Trp Asn Gly
1               5                   10                  15

Ile Pro Leu Ser Met Glu Leu Asn Leu Trp Asn Ile Lys Glu Tyr Ser
                20                  25                  30

Gly Ser Val Ala Met Lys Phe Asp Gly Glu Lys Ile Thr Phe Asp Ala
            35                  40                  45

Asp Ile Gln Asn Leu Ser Pro Lys Glu Pro Glu Arg Tyr Val Leu Gly
        50                  55                  60

Tyr Pro Glu Phe Tyr Tyr Gly Tyr Lys Pro Trp Glu Asn His Thr Ala
65                  70                  75                  80

Glu Gly Ser Lys Leu Pro Val Pro Val Ser Ser Met Lys Ser Phe Ser
                85                  90                  95

Val Glu Val Ser Phe Asp Ile His His Glu Pro Ser Leu Pro Leu Asn
                100                 105                 110

Phe Ala Met Glu Thr Trp Leu Thr Arg Glu Lys Tyr Gln Thr Glu Ala
            115                 120                 125

Ser Ile Gly Asp Val Glu Ile Met Val Trp Phe Tyr Phe Asn Asn Leu
        130                 135                 140

Thr Pro Gly Gly Glu Lys Ile Glu Glu Phe Thr Ile Pro Phe Val Leu
145                 150                 155                 160

Asn Gly Glu Ser Val Glu Gly Thr Trp Glu Leu Trp Leu Ala Glu Trp
                165                 170                 175

Gly Trp Asp Tyr Leu Ala Phe Arg Leu Lys Asp Pro Val Lys Lys Gly
            180                 185                 190

Arg Val Lys Phe Asp Val Arg His Phe Leu Asp Ala Ala Gly Lys Ala
        195                 200                 205

Leu Ser Ser Ser Ala Arg Val Lys Asp Phe Glu Asp Leu Tyr Phe Thr
    210                 215                 220
```

Val Trp Glu Ile Gly Thr Glu Phe Gly Ser Pro Glu Thr Lys Ser Ala
225                 230                 235                 240

Gln Phe Gly Trp Lys Phe Glu Asn Phe Ser Ile Asp Leu Glu Val Arg
            245                 250                 255

Glu

<210> SEQ ID NO 3
<211> LENGTH: 774
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 3
atggtactga tgacaaaacc gggaacatcg gattttgtat ggaatggcat tccccttcc        60 atggagctga atctgtggaa cataaaggaa tactccggtt ctgtagctat gaaattcgac      120
ggtgaaaaga taactttcga tgcggacatt cagaatcttt ctccgaaaga accgaaagg       180 tttgttctcg ttatcccga gttttattac ggttacaaac catgggaaaa tcacacagca      240
gaaggttcga aacttccggt accagtttct tctatgaaat cattttccgt cgaagtttct      300
ttcgatattc accacgaacc gtctctgcct ttgaactttg ccatggaaac atggctcaca      360
agagaaaagt accagacgga agcatcgatc ggcgatgttg aaatcatggt ctggttctat      420
ttcaacaatc tcacacccgg aggcgaaaag atagaagagt tcacgatccc gttcgtgctg      480
aacggagaga gtgtcgaagg cacctgggaa ctgtggctcg cggagtgggg atgggactac      540
ctcgctttcc gcttgaagga tcccgtgaag aagggaaggg tgaagttcga cgtgaggcat      600
tttcttgatg ccgccggaaa agctctttcg agttctgctc gagtgaaaga ttttgaagat      660
ctttacttca ccgtctggga atcggaacc gagtttggaa gtccggaaac aaaaagtgca      720
cagttcgggt ggaagtttga aaacttctct attgatctgg aggtgagaga atga           774

<210> SEQ ID NO 4
<211> LENGTH: 257
<212> TYPE: PRT
<213> ORGANISM: Artificial Sequence
<220> FEATURE:
<223> OTHER INFORMATION: Sequence synthetically translated from SEQ. ID.
      NO: 3

<400> SEQUENCE: 4

Met Val Leu Met Thr Lys Pro Gly Thr Ser Asp Phe Val Trp Asn Gly
1               5                   10                  15

Ile Pro Leu Ser Met Glu Leu Asn Leu Trp Asn Ile Lys Glu Tyr Ser
            20                  25                  30

Gly Ser Val Ala Met Lys Phe Asp Gly Glu Lys Ile Thr Phe Asp Ala
        35                  40                  45

Asp Ile Gln Asn Leu Ser Pro Lys Glu Pro Glu Arg Phe Val Leu Gly
    50                  55                  60

Tyr Pro Glu Phe Tyr Tyr Gly Tyr Lys Pro Trp Glu Asn His Thr Ala
65                  70                  75                  80

Glu Gly Ser Lys Leu Pro Val Pro Val Ser Ser Met Lys Ser Phe Ser
            85                  90                  95

Val Glu Val Ser Phe Asp Ile His His Glu Pro Ser Leu Pro Leu Asn
            100                 105                 110

Phe Ala Met Glu Thr Trp Leu Thr Arg Glu Lys Tyr Gln Thr Glu Ala
        115                 120                 125

```
Ser Ile Gly Asp Val Glu Ile Met Val Trp Phe Tyr Phe Asn Asn Leu
130                 135                 140
Thr Pro Gly Gly Glu Lys Ile Glu Glu Phe Thr Ile Pro Phe Val Leu
145                 150                 155                 160
Asn Gly Glu Ser Val Glu Gly Thr Trp Glu Leu Trp Leu Ala Glu Trp
                165                 170                 175
Gly Trp Asp Tyr Leu Ala Phe Arg Leu Lys Asp Pro Val Lys Lys Gly
                180                 185                 190
Arg Val Lys Phe Asp Val Arg His Phe Leu Asp Ala Ala Gly Lys Ala
                195                 200                 205
Leu Ser Ser Ser Ala Arg Val Lys Asp Phe Glu Asp Leu Tyr Phe Thr
210                 215                 220
Val Trp Glu Ile Gly Thr Glu Phe Gly Ser Pro Glu Thr Lys Ser Ala
225                 230                 235                 240
Gln Phe Gly Trp Lys Phe Glu Asn Phe Ser Ile Asp Leu Glu Val Arg
                245                 250                 255
Glu
```

<210> SEQ ID NO 5
<211> LENGTH: 774
<212> TYPE: DNA
<213> ORGANISM: Artificial Sequence
<220> FEATURE:
<223> OTHER INFORMATION: Synthetically generated DNA encoding a modified enzyme

<400> SEQUENCE: 5

```
atggtactga tgacaaaacc gggaacatcg gattttgtat ggaatggcat tccccttccc    60
atggagctga atctgtggaa cataaaggaa tactccggtt ctgtagctat gaaattcgac   120
ggtgaaaaga taactttcga tgcggacatt cagaatcttt ctccgaaaga accggaaagg   180
gccgttctcg gttatcccga gttttattac ggttacaaac catgggaaaa tcacacagca   240
gaaggttcga acttccggt accagtttct tctatgaaat cattttccgt cgaagtttct   300
ttcgatattc accacgaacc gtctctgcct ttgaactttg ccatggaaac atggctcaca   360
agagaaaagt accagacgga agcatcgatc ggcgatgttg aaatcatggt ctggttctat   420
ttcaacaatc tcacacccgg aggcgaaaag atagaagagt tcacgatccc gttcgtgctg   480
aacggagaga gtgtcgaagg cacctgggaa ctgtggctcg cggagtgggg atgggactac   540
ctcgctttcc gcttgaagga tcccgtgaag aagggaaggg tgaagttcga cgtgaggcat   600
tttcttgatg ccgccggaaa agctctttcg agttctgctc gagtgaaaga ttttgaagat   660
ctttacttca ccgtctggga aatcggaacc gagtttggaa gtccggaaac aaaaagtgca   720
cagttcgggt ggaagtttga aaacttctct attgatctgg aggtgagaga atga         774
```

<210> SEQ ID NO 6
<211> LENGTH: 257
<212> TYPE: PRT
<213> ORGANISM: Artificial Sequence
<220> FEATURE:
<223> OTHER INFORMATION: Sequence synthetically translated from SEQ. ID. NO: 5

<400> SEQUENCE: 6

```
Met Val Leu Met Thr Lys Pro Gly Thr Ser Asp Phe Val Trp Asn Gly
1               5                   10                  15
Ile Pro Leu Ser Met Glu Leu Asn Leu Trp Asn Ile Lys Glu Tyr Ser
                20                  25                  30
```

```
Gly Ser Val Ala Met Lys Phe Asp Gly Glu Lys Ile Thr Phe Asp Ala
            35                  40                  45

Asp Ile Gln Asn Leu Ser Pro Lys Glu Pro Glu Arg Ala Val Leu Gly
     50                  55                  60

Tyr Pro Glu Phe Tyr Tyr Gly Tyr Lys Pro Trp Glu Asn His Thr Ala
 65                  70                  75                  80

Glu Gly Ser Lys Leu Pro Val Pro Val Ser Ser Met Lys Ser Phe Ser
                 85                  90                  95

Val Glu Val Ser Phe Asp Ile His His Glu Pro Ser Leu Pro Leu Asn
            100                 105                 110

Phe Ala Met Glu Thr Trp Leu Thr Arg Glu Lys Tyr Gln Thr Glu Ala
        115                 120                 125

Ser Ile Gly Asp Val Glu Ile Met Val Trp Phe Tyr Phe Asn Asn Leu
    130                 135                 140

Thr Pro Gly Gly Glu Lys Ile Glu Glu Phe Thr Ile Pro Phe Val Leu
145                 150                 155                 160

Asn Gly Glu Ser Val Glu Gly Thr Trp Glu Leu Trp Leu Ala Glu Trp
                165                 170                 175

Gly Trp Asp Tyr Leu Ala Phe Arg Leu Lys Asp Pro Val Lys Lys Gly
            180                 185                 190

Arg Val Lys Phe Asp Val Arg His Phe Leu Asp Ala Ala Gly Lys Ala
        195                 200                 205

Leu Ser Ser Ser Ala Arg Val Lys Asp Phe Glu Asp Leu Tyr Phe Thr
    210                 215                 220

Val Trp Glu Ile Gly Thr Glu Phe Gly Ser Pro Glu Thr Lys Ser Ala
225                 230                 235                 240

Gln Phe Gly Trp Lys Phe Glu Asn Phe Ser Ile Asp Leu Glu Val Arg
                245                 250                 255

Glu

<210> SEQ ID NO 7
<211> LENGTH: 774
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 7
atggtactga tgacaaaacc gggaacatcg gattttgtat ggaatggcat tccccttccc      60
atggagctga atctgtggaa cataaaggaa tactccggtt ctgtagctat gaaattcgac     120
ggtgaaaaga taactttcga tgcggacatt cagaatcttt ctccgaaaga accggaaagg     180
ggtgttctcg gttatcccga gttttattac ggttacaaac catgggaaaa tcacacagca     240
gaaggttcga aacttccggt accagttcct tctatgaaat cattttccgt cgaagtttct     300
ttcgatattc accacgaacc gtctctgcct ttgaactttg ccatgaaaac atggctcaca     360
agagaaaagt accagacgga agcatcgatc ggcgatgttg aaatcatggt ctggttctat     420
ttcaacaatc tcacacccgg aggcgaaaag atagaagagt tcacgatccc gttcgtgctg     480
aacggagaga gtgtcgaagg cacctgggaa ctgtggctcg cggagtgggg atgggactac     540
ctcgctttcc gcttgaagga tcccgtgaag aagggaaggg tgaagttcga cgtgaggcat     600
tttcttgatg ccgccggaaa agctcttttcg agttctgctc gagtgaaaga ttttgaagat     660 cttttacttca ccgtctggga aatcggaacc gagtttggaa gtccggaaac aaaaagtgca     720
cagttcgggt ggaagtttga aaacttctct attgatctgg aggtgagaga atga           774
```

```
<210> SEQ ID NO 8
<211> LENGTH: 257
<212> TYPE: PRT
<213> ORGANISM: Artificial Sequence
<220> FEATURE:
<223> OTHER INFORMATION: Sequence synthetically translated from SEQ. ID.
      NO: 7

<400> SEQUENCE: 8

Met Val Leu Met Thr Lys Pro Gly Thr Ser Asp Phe Val Trp Asn Gly
1               5                   10                  15

Ile Pro Leu Ser Met Glu Leu Asn Leu Trp Asn Ile Lys Glu Tyr Ser
                20                  25                  30

Gly Ser Val Ala Met Lys Phe Asp Gly Glu Lys Ile Thr Phe Asp Ala
            35                  40                  45

Asp Ile Gln Asn Leu Ser Pro Lys Glu Pro Glu Arg Gly Val Leu Gly
        50                  55                  60

Tyr Pro Glu Phe Tyr Tyr Gly Tyr Lys Pro Trp Glu Asn His Thr Ala
65                  70                  75                  80

Glu Gly Ser Lys Leu Pro Val Pro Val Ser Ser Met Lys Ser Phe Ser
                85                  90                  95

Val Glu Val Ser Phe Asp Ile His His Glu Pro Ser Leu Pro Leu Asn
                100                 105                 110

Phe Ala Met Glu Thr Trp Leu Thr Arg Glu Lys Tyr Gln Thr Glu Ala
            115                 120                 125

Ser Ile Gly Asp Val Glu Ile Met Val Trp Phe Tyr Phe Asn Asn Leu
        130                 135                 140

Thr Pro Gly Gly Glu Lys Ile Glu Glu Phe Thr Ile Pro Phe Val Leu
145                 150                 155                 160

Asn Gly Glu Ser Val Glu Gly Thr Trp Glu Leu Trp Leu Ala Glu Trp
                165                 170                 175

Gly Trp Asp Tyr Leu Ala Phe Arg Leu Lys Asp Pro Val Lys Lys Gly
            180                 185                 190

Arg Val Lys Phe Asp Val Arg His Phe Leu Asp Ala Ala Gly Lys Ala
                195                 200                 205

Leu Ser Ser Ser Ala Arg Val Lys Asp Phe Glu Asp Leu Tyr Phe Thr
        210                 215                 220

Val Trp Glu Ile Gly Thr Glu Phe Gly Ser Pro Glu Thr Lys Ser Ala
225                 230                 235                 240

Gln Phe Gly Trp Lys Phe Glu Asn Phe Ser Ile Asp Leu Glu Val Arg
                245                 250                 255

Glu
```

THERMOSTABLE CELLULASE HAVING INCREASED ENZYME ACTIVITY

FIELD OF THE INVENTION

The present invention relates to a cellulase, and more particularly to a thermostable cellulase.

BACKGROUND OF THE INVENTION

Cellulose is one of the major components in plant cell wall and is also a major resource of biomass on earth. Hence, many enzymes that degrade cellulose can be widely applied in many different industries. Cellulose is a polysaccharide composed of glucose units linking by β-1,4-glycosidic bond. These polysaccharides organize tightly together to form crystalline cellulose in order to defense destructing energy from outside of plant. On the other hand, many kinds of herbivores and microbes need to degrade cellulose from plant to glucose as an energy source by different degrading enzymes including cellulase, xylanase and so on. The catalytic mechanism of cellulase involves hydrolyzing the β-1,4-glycosidic bond between two sugar units by acid-base interaction. Cellulase can be generally divided into three groups including endoglucanase, cellobiohydrolase and β-glucosidase. Endoglucanase can randomly degrade polysaccharide cellulose into many small fragments. Cellobiohydrolase can degrade polysaccharide from reducing end or non-reducing end to release main product, cellobiose. β-Glucosidase can degrade cellobiose into simple sugar glucose.

So far, the industrial applications of cellulase are widespread in food industry, feed industry, textile industry or paper pulp industry, even in biofuel production. In general, cellulase needs to conform to different appropriate conditions according to different industrial needs. For example, acidic and thermostable enzymes are suitable for the feed industry but textile industry prefers alkaline enzymes. Therefore, scientists always try to seek better enzymes which are more suitable for different industrial needs in academic or industrial researches. Currently, many researchers and enzyme companies could produce better enzymes by screening in nature or modifying present enzymes. There are generally two strategies of enzyme modification including directed evolution that randomly mutates the enzyme gene and selects with desirable properties or rationale engineering that specifically mutates the enzyme gene based on the structural information of the enzyme.

Different industrial production processes need different appropriate enzymes to cooperate and participate in their production procedures. Despite cellulase has been applied in industry for a long time, many industrial cellulases which are produced from mesophile such as *Trichoderma reesei* have worse thermostabilities. On the other hand, thermostable cellulase can be efficiently applied in the industry which needs high temperature reaction condition, such as brewing, bioethanol production and so on. Thermostable enzyme has higher protein stability, so it can be stable and even work better in high temperature condition. In addition, to increase enzyme activity is also a key point for the improvement of industrial enzyme. Higher enzyme activity represents the cost down and the companies will have better profit.

Therefore, the present invention improves the enzyme activity by site-directed mutagenesis of the gene to reduce the cost of enzyme productions.

SUMMARY OF THE INVENTION

An object of the present invention is to modify a thermostable cellualse by means of structural analysis and site-directed mutagenesis to efficiently increase the enzyme activity, enhance the industrial value and reduce the production costs.

According to an aspect of the present invention, there is provided a cellulase comprising a modified amino acid sequence of SEQ ID NO: 2, wherein the tyrosine at position 61 is substituted with an amino acid selected from the group consisting of phenylalanine, alanine and glycine.

In an embodiment, a gene encoding the amino acid sequence of SEQ ID NO: 2 is Cel 12A gene isolated from *Thermotoga maritima*. The cellulase is a β-1,4-endoglucanase and is a thermostable cellulase.

In an embodiment, the cellulase comprises an amino acid sequence of SEQ ID NO: 4.

In an embodiment, the cellulase comprises an amino acid sequence of SEQ ID NO: 6.

In an embodiment, the cellulase comprises an amino acid sequence of SEQ ID NO: 8.

According to another aspect of the present invention, there is provided a nucleic acid encoding the aforesaid cellulase, and a recombinant plasmid comprising the aforesaid nucleic acid.

According to an additional aspect of the present invention, there is provided an industrial use of the aforesaid cellulase, wherein the industrial use comprises uses in food industry, feed industry, textile industry, paper pulp industry and biofuel industry.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the gene sequence and amino acid sequence of wild type Cel12A;

FIGS. 2A to 2C show the protein structures of Cel 12A solved by X-ray crystallography;

FIG. 3 shows the sequences of mutagenic primers for the Y61F, Y61A and Y61G mutants.

FIG. 4 shows the gene sequence and amino acid sequence of the Y61F mutant;

FIG. 5 shows the gene sequence and amino acid sequence of the Y61A mutant;

FIG. 6 shows the gene sequence and amino acid sequence of the Y61G mutant;

DETAILED DESCRIPTION OF THE PREFERRED EMBODIMENT

Figure 7:
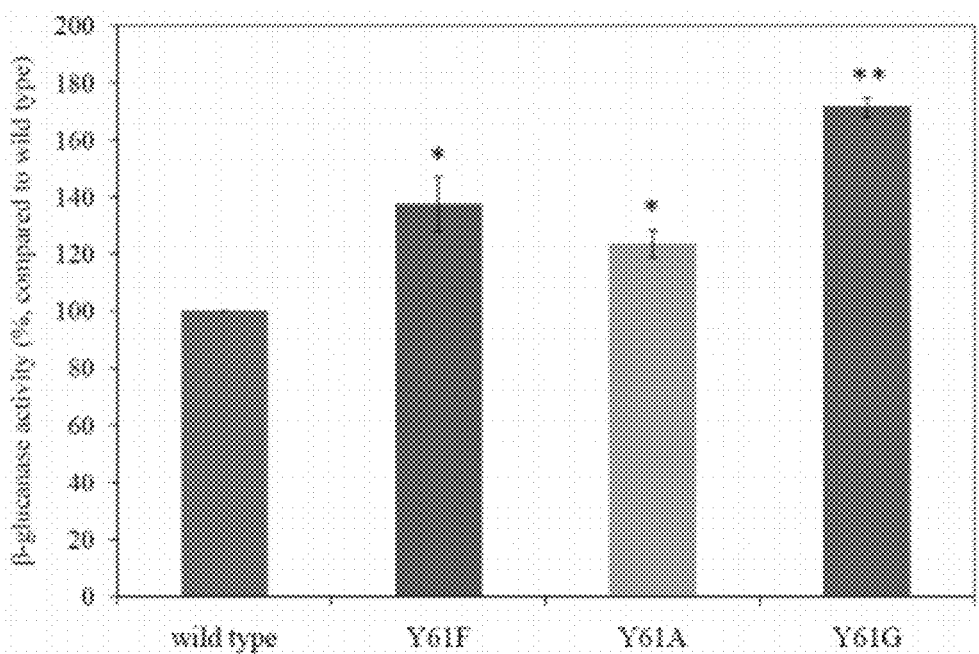
FIG. 7 shows the cellulase activity analysis of the wild type Cel 12A protein and the Y61F, Y61A and Y61G mutants.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, a gene of Cel 12A, which encodes a protein of β-1,4-endoglucanase, was isolated from a hyperthermostable microorganism, *Thermotoga maritima*. This thermostable cellulase has high potential industrial application, especially in the industries which need the reaction conditions at high temperature. For improving and broadening the industrial applications of this thermostable cellulase, the cellulase protein structure in complex with its substrates was solved by X-ray crystallography first, and then the active site residues involved in catalysis and substrate interactions were analyzed. Subsequently, the site-directed mutagenesis of some important residues that were chosen from structural information was performed to obtain high cellulase activity mutants. The enzyme modification process of this thermostable cellulase is described in detail as follows.

First, the Cel12A gene from *Thermotoga maritima* (Genbank: CAA93273) was selected as the target gene. As shown in FIG. 1, the full length of sequence of the Cel12A gene is 774 base pairs (SEQ ID NO: 1), which encodes a protein of 257 amino acids (SEQ ID NO: 2). The Cel12A gene was constructed into pET16b vector by XbaI and NdeI. Besides, the N-terminus of the Cel12A gene was fused with six Histidines for the purification purpose. The primers for polymerase chain reaction were 5'-GCTCTAGAAATAATTTTG TTTAACTTTAAGAAGGAGATATACCATGGGCCA CCA CCACCACCACCACATGGTACTGATGACAAAA—3' (forward primer) and 5'-GGAATTCCA TATGTTATCAT-TCTCTCACCTCCAGATCAAT—3' (reverse primer). The constructed Cel12A pET16b plasmid was transformed into *E. coli* BL21 (DE3) competent cell and the transformed strains were screened by LB plate with 100 µg/ml Ampicillin. The transformed strain was inoculated and cultured into 5 ml LB medium and then amplified into 200 ml LB medium. Finally, the culture was grown into 6 L LB medium and incubated at 37° C. until OD600 reached 0.6-0.8. The protein expression was induced by adding 1 mM IPTG for two days. After that, the cells were collected by centrifugation at 6000 rpm for 10 min. The cells were lysed by sonicator and then centrifuged at 16000 rpm for 30 min to collect supernatants for purification. For the high purity of Cel12A protein, the Cel12A protein was purified by FPLC system using $Ni^{2+}$ column and DEAE column. Finally, the Cel12A protein, which had above 95% purity, was concentrated up to 5 mg/ml in protein buffer (25 mM Tris and 150 mM NaCl, pH 7.5) and then was stored at −80° C. for further experiment need.

To solve the protein structure of Cel12A by X-ray crystallography, the protein crystal was obtained by using sitting drop vapor diffusion method at room temperature. The crystal was first seen from crystal screen kits and the better crystal was obtained by a condition composed of 0.2 M Ammonium sulfate, 25% w/v PEG3350 and 0.1 M Bis-Tris, pH 5.5 at room temperature for two days. In addition, the phase problem was solved by multiple isomorphous replacement (MIR) method. Basically, the protein crystals were soaked with some different mercury derivatives and then the different diffraction data were collected and processed. The protein structure of Cel 12A was subsequently determined and refined by crystallographic software of Solve/Resolve, CNS and XtalView. Furthermore, the structures of Cel12A in complex with cellobiose and cellotetraose were determined by soaking the crystals with cellobiose and cellotetraose.

FIGS. 2A to 2C show the protein structures of Cel12A solved by X-ray crystallography, including apo form and substrate binding complex form. The protein structure of Cel12A belongs to β-jellyroll protein fold which mainly composed of two β-sheets (as shown in FIG. 2A). The cleft of the protein structure is the active site which allows substrate binding (as shown in FIG. 2B). There are two crucial amino acids in the active site, including Arg60 and Tyr61 that interact with the sugar substrates (as shown in FIG. 2C, and the substrate cellotetraose was shown here). From the Ramachandran plot, the Tyr61 is adapted in a disallowed region. Moreover, Arg60 and Tyr61 both interacted with the substrates (cellobiose and cellotetraose) and were seem very important for the enzyme catalysis reaction. Therefore, Tyr61 was mutated to several different amino acids in order to obtain high cellulase activity mutants.

Figures 5, 6:
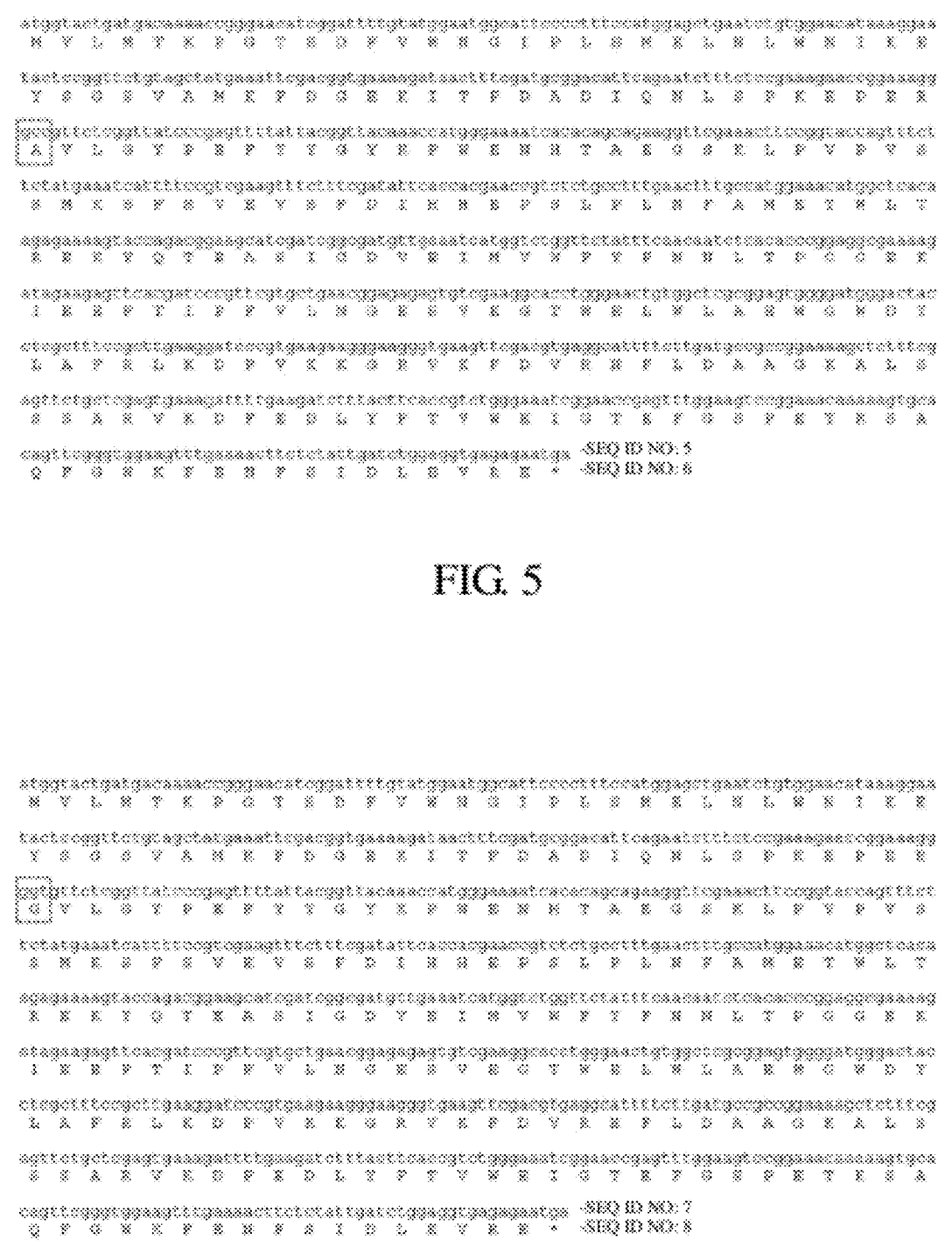

The Cel12A mutants, including Y61F, Y61A and Y61G were obtained by site-directed mutagenesis. The sequences of mutagenic primers for these mutants were listed in FIG. 3. The mutant plasmids were transformed into *E. coli* and the mutant genes were confirmed by sequencing. FIGS. 4 to 6 show the mutant gene sequence and amino acid sequence of Cel12A/Y61F, Cel12A/Y61A and Cel12A/Y61G, respectively, wherein the gene sequences were numbered as SEQ ID NO: 3, SEQ ID NO: 5, SEQ ID NO: 7, and the amino acid sequences were numbered as SEQ ID NO: 4, SEQ ID NO: 6, SEQ ID NO: 8, respectively. The mutant genes were transformed into *E. coli* and the mutant proteins were further expressed and purified by the same procedures as those for the wild type Cel12A protein.

The cellulase activity assay was modified from the previous study (Konig, J., Grasser, R., Pikor, H., and Vogel, K. (2002) *Anal Bioanal Chem* 374, 80-87). In general, the proper concentration of protein solution was mixed with 1% β-glucan substrate on equal proportion and was incubated at 85° C. for 10 min. The mixed solution was added with 1% DNS solution and then incubated at 100° C. boiled water for 5 min. The absorption of OD540 was detected and the enzyme activity was obtained. The standard curve of enzyme activity was determined by 0-0.25 mg/ml glucose standard solution. One unit was defined as the enzyme level that could release 1 µmole product per minute.

FIG. 7 shows the cellulase activity analysis of the wild type Cel12A protein and the Y61F, Y61A and Y61G mutants. 150 ng/ml proteins were used and incubated at 85° C. for 10 min with 1% β-glucan as substrate. The cellulase activity of the wild type Cel12A protein was set to 100%. The standard error of the mean (SEM) was also shown in the figure. Two-tailed P values were determined by an unpaired Student's t-test, wherein one star (*) represents $P<0.05$ and two stars (**) represents $P<0.001$. It is observed that the specific activities (unit/mg) of Y61F, Y61A and Y61G mutants were all higher than the wild type enzyme significantly; that is to say, if Tyr61 was mutated to phenylalanine, alanine and glycine, the cellulase specific activities become better than the wild-type enzyme. Especially, the activity of Y61G mutant was more than 1.7-fold when compared with the wild type enzyme.

Figure 8:
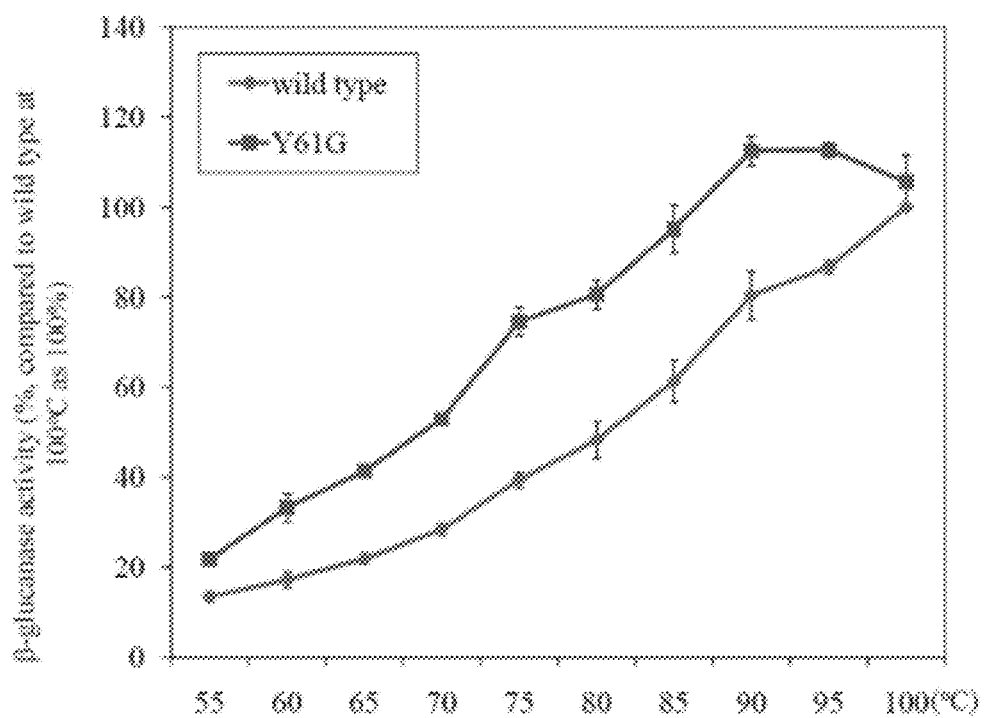
FIG. 8 shows the optimal temperature analysis of the wild type Cel 12A protein and the Y61G mutant.

For the optimal temperature analysis, the enzyme protein samples were incubated for 10 min at different temperatures that were between 55° C. and 100° C., and the enzyme activities were analyzed as aforesaid procedures. FIG. 8 shows the optimal temperature analysis of the wild type Cel 12A protein and the Y61G mutant. In this assay, 150 ng/ml proteins were used and incubated at different working temperatures for 10 min with 1% β-glucan as substrate. The cellulase activity of the wild type Cel12A protein at 100° C. was set to 100% and the activities for the Y61G mutant and the wild-type enzyme at different temperatures were shown. The standard error of the mean (SEM) was also shown in the figure. It is observed that, for the optimal temperature analysis, there is almost no difference on optimal temperature between the wild-type enzyme and the Y61G mutant. Furthermore, the cellulase activity of Y61G mutant was significantly higher than the wild type enzyme at every measured temperature points when using the same protein concentration in the assay conditions. The range of optimal temperature of Y61G mutant was broader than the wild type enzyme. For example, the wild type enzyme has 50% activity at 80° C., but the Y61G mutant still has 50% activity at 70° C. These results indicated that one point mutation (Y61G) not only increased significantly the cellulase activity at every measured temperature points, but also retain the thermostability (still function very well at the temperature above 95° C.).

To test if the Cel12A protein can be expressed well in industrial expression system, *Pichia pastoris* expression system was used. The Cel12A wild-type gene and the Y61G mutant genes were cloned into pPICZαA vector by EcoRI and NotI. Each plasmid DNA was further linearized by PmeI and transformed into *Pichia* via electroporation. The transformed cells were then selected on YPD plate with 100 μg/ml zeocin at 30° C. for two days. The picked colonies were inoculated into 5 ml YPD medium at 30° C. overnight and further amplified into 50 ml BMGY medium at 30° C. overnight. After that, the cultured medium was changed to 20 ml BMMY with 0.5% methanol to induce the target protein expression. The samples were collected at different time points for every 24 hours and at that time 0.5% methanol was added, too. The samples were then centrifuged to collect supernatants and the cellulase activities were detected using the procedure mentioned above. As a result, the total cellulase activity of Y61G mutant was significantly higher (2.2-fold increase) than that of the wild type enzyme. The expression level of the wild type enzyme and Y61G mutant were almost identical in *Pichia pastoris*. Therefore, the higher total cellulase activity of Y61G mutant was not caused by the protein production amount, but caused by the enzyme specific activity. This result was concord with the result obtained from *E. coli*.

To test if the cellulase can be mass produced by industrial scale of fermentation, the transformed cells were inoculated into 5 ml YPD medium at 30° C. overnight. Then, the culture was amplified into 2 L YPD medium and further transferred to 19 L fermentation medium (FBSM) in a 50 L fermentor. The manipulation of *Pichia* fermentation was generally followed with the guideline from Invitrogen. During fermentation process, temperature was maintained at 30° C. and pH was fixed to 5.0 by adding ammonium hydroxide. Dissolved oxygen was maintained above 40% by air flow rate and agitation rate. After batch phase, the carbon source was added by feeding 50% glycerol. Methanol was added to induce the protein expression. The protein expression yield and cellulase activity were monitored for every 12 hours. Consequently, the cellulase activity of the Y61G mutant was higher (up to 2-fold) than that of the wild type enzyme after protein induction for 120 hours.

In conclusion, to further investigate and modify the thermostable cellulase Cel12A, the protein structures of Cel12A were solved by X-ray crystallography. From the structure analysis, Tyr61 was assumed to play an important role in enzyme catalysis reaction of Cel 12A. Therefore, Tyr61 was mutated to several different amino acids, including phenylalanine, alanine and glycine, and it was found the cellulase specific activities of Y61F, Y61A and Y61G mutants became better than that of the wild-type enzyme. Especially, the activity of the Y61G mutant was significantly higher (up to 2-fold) than the wild type enzyme, and the Y61G mutant still retain its temperature optimum above 95° C. and even broaden the working temperature range. Except the *E. coli* expression system, the Y61G mutant also had better cellulase activity in the industrial used yeast strain, *Pichia pastoris*, by using flask and 50 L fermentor test. Therefore, the Y61G mutant is of much value to reduce the production cost and will has more industrial potential especially those industries that involved in using thermostable cellulase.

Further, the application fields of cellulase in industry are widespread, for example, food industry, feed industry, textile industry, paper pulp industry and biofuel industry. For the food industry, like juice production, the degradation of pectin that largely existed in fruit is crucial but is often interfered by cellulose which co-existed with the pectin. Hence, cellulase can be added with pectinase to assist fruit degradation and further improves juice clearance in the juice production process. Besides, cellulase can efficiently degrade raw materials like barley or wheat in the saccharification step of brewing industry which is often in high temperature conditions that thermostable cellulase such as TmCel12A might be more suitable. For feed industry, liquid cellulase can be spurted on bran carriers and mixed with feed to help animals degrade feed containing large cellulose and improve the digestion and absorption of cellulose in animal bowels. As for textile industry, cellulase can be applied to the post-processing of textiles. For example, cellulase can work on the surface of textiles like biopolishing to cotton textiles that can improve glossiness and handfeel and biostoning to denim fabric that can unevenly eliminate stains and further cause color-washing effect. Thermostable cellulase is also more suitable for paper pulp industry and its application can be divided into two parts. One is that cellulase can degrade materials like wood in the process of pulp production. Besides, cellulase can efficiently eliminate ink on waste paper in the process of resource recycling. As for biofuel industry, thermostable cellulase is suitable for the pre-treatment process that is mainly a heat treatment to plant cellulose materials. Cellulase can efficiently degrade cellulose materials to simple sugars which can be used by microbes in the saccharification process. Then, the microbes can utilize simple sugars by fermentation to largely produce bioethanol. From the above, cellulase can be applied to many different industries but most commercial cellulases now are not suitable at high temperature reaction conditions. Therefore, since the Y61F, Y61A and Y61G mutants of the Cel12A protein provided in the present invention have significantly increased cellulase activities at high temperature, they can be suitably used in food industry, feed industry, textile industry, paper pulp industry and biofuel industry, so the present invention possesses high industrial value.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cellulase comprising a modified amino acid sequence of SEQ ID NO: 2, wherein the modification is substitution of tyrosine at position 61 with an amino acid selected from the group consisting of phenylalanine, alanine and glycine.

2. The cellulase according to claim 1 wherein the amino acid sequence of SEQ ID NO: 2 is encoded by Cel12A gene isolated from *Thermotoga maritima*.

3. The cellulase according to claim 1 being a β-1,4-endoglucanase.

4. The cellulase according to claim 1 being a thermostable cellulase.

5. The cellulase according to claim 1 comprising the amino acid sequence of SEQ ID NO: 4.

6. The cellulase according to claim 1 comprising the amino acid sequence of SEQ ID NO: 6.

7. The cellulase according to claim 1 comprising the amino acid sequence of SEQ ID NO: 8.

* * * * *